(12) United States Patent
Morishita

(10) Patent No.: US 10,105,096 B2
(45) Date of Patent: Oct. 23, 2018

(54) BIOLOGICAL OBSERVATION APPARATUS

(71) Applicant: OLYMPUS CORPORATION, Tokyo (JP)

(72) Inventor: Koki Morishita, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 990 days.

(21) Appl. No.: 14/321,978

(22) Filed: Jul. 2, 2014

(65) Prior Publication Data

US 2014/0316279 A1    Oct. 23, 2014

Related U.S. Application Data

(63) Continuation of application No. PCT/JP2013/052232, filed on Jan. 31, 2013.

(30) Foreign Application Priority Data

Jan. 31, 2012  (JP) ................................ 2012-018129

(51) Int. Cl.
*A61B 5/00* (2006.01)
*A61B 1/00* (2006.01)
*A61B 1/06* (2006.01)

(52) U.S. Cl.
CPC .......... *A61B 5/4887* (2013.01); *A61B 1/0005* (2013.01); *A61B 1/00009* (2013.01);
(Continued)

(58) Field of Classification Search
CPC ............................. A61B 18/203; A61N 5/062
See application file for complete search history.

(56) References Cited

U.S. PATENT DOCUMENTS

| 4,997,769 A * | 3/1991 | Lundsgaard ........... G01N 21/31 |
| | | 356/328 |
| 6,452,188 B1 * | 9/2002 | Chubb ................. A61B 5/0059 |
| | | 250/338.1 |

(Continued)

FOREIGN PATENT DOCUMENTS

| EP | 2 810 596 A1 | 12/2014 |
| JP | H01-217415 A | 8/1989 |

(Continued)

OTHER PUBLICATIONS

International Search Report dated Jun. 2, 2015 in related International Patent Application No. PCT/JP2015/056297, together with English language translation.

(Continued)

*Primary Examiner* — Michael D Abreu
(74) *Attorney, Agent, or Firm* — Scully, Scott, Murphy & Presser, P.C.

(57) ABSTRACT

Provided is a biological observation apparatus including irradiating portions that radiate illumination light onto biological tissue, an imaging portion that, of reflected light reflected at the biological tissue due to the illumination light radiated by the irradiating portions, captures reflected light in a wavelength band in which an absorption characteristic of β-carotene is greater than an absorption characteristic of hemoglobin, thus acquiring a reflected-light image, and a display portion that displays the reflected-light image acquired by the imaging portion.

10 Claims, 11 Drawing Sheets

(52) U.S. Cl.
CPC .......... *A61B 1/0638* (2013.01); *A61B 5/0062* (2013.01); *A61B 5/742* (2013.01)

(56) References Cited

U.S. PATENT DOCUMENTS

| | | | |
|---|---|---|---|
| 2003/0216795 A1* | 11/2003 | Harth .................... | A61N 5/062 |
| | | | 607/88 |
| 2007/0038124 A1 | 2/2007 | Fulghum, Jr. et al. | |
| 2007/0197884 A1* | 8/2007 | Bornstein ............ | A61N 5/0613 |
| | | | 600/310 |
| 2009/0322863 A1 | 12/2009 | Takahashi | |
| 2010/0082019 A1* | 4/2010 | Neev .................... | A61B 18/203 |
| | | | 606/9 |
| 2011/0254937 A1 | 10/2011 | Yoshino | |
| 2012/0302892 A1* | 11/2012 | Lue ..................... | A61B 5/0071 |
| | | | 600/476 |
| 2013/0147400 A1* | 6/2013 | Van Herpen .......... | A61B 90/35 |
| | | | 315/313 |

FOREIGN PATENT DOCUMENTS

| | | |
|---|---|---|
| JP | 2007-282965 A | 11/2007 |
| JP | 2010-115341 A | 5/2010 |
| JP | 2011-218090 A | 11/2011 |
| JP | 2011-224038 A | 11/2011 |
| WO | WO 2010/116902 A1 | 10/2010 |
| WO | 2013/100030 A1 | 7/2013 |
| WO | 2013/115323 A1 | 8/2013 |

OTHER PUBLICATIONS

Extended Supplementary European Search Report dated Jul. 16, 2015 in related European Patent Application No. 13 74 4253.9.
International Search Report dated Apr. 23, 2013 issued in PCT/JP2013/052232.

* cited by examiner

BIOLOGICAL OBSERVATION APPARATUS

CROSS-REFERENCE TO RELATED APPLICATIONS

This is a continuation of International Application PCT/JP2013/052232, with an international filing date of Jan. 31, 2013, which is hereby incorporated by reference herein in its entirety. This application claims the benefit of Japanese Patent Application No. 2012-018129, the contents of which are incorporated herein by reference.

TECHNICAL FIELD

The present invention relates to a biological observation apparatus.

BACKGROUND ART

Narrow Band Imaging (NBI) has been known in the related art; in NBI, illumination light in a wavelength that is converted to a narrow band and that tends to be absorbed by hemoglobin contained in blood is radiated, and a capillary or the like at the mucosa surface is displayed with emphasis (for example, see Patent Literature 1).

It is expected that this Narrow Band Imaging will serve as an alternative observation method to dye-spraying which is widely used for detailed diagnosis of esophagus regions and pit pattern (ductal structure) observation of the large intestine, and it is also expected that NBI will contribute to realizing more efficient examination by reducing examination time and the incidence of unnecessary biopsies.

CITATION LIST

Patent Literature

{Patent Literature 1} Japanese Unexamined Patent Application, Publication No. 2011-224038

SUMMARY OF INVENTION

The present invention provides a biological observation apparatus with which the tissue structure at a surface of a target organ or the like to be removed can be made easier to view, and with which nerves surrounding the target organ can be prevented from being damaged.

An aspect of the present invention provides a biological observation apparatus for performing surgical treatment, including an optical-image forming part for forming an optical image in which, by using a difference in an optical characteristic between an adipose layer and surrounding tissue of the adipose layer in a specific portion, a region including the adipose layer, which contains a greater number of nerves relative to the surrounding tissue, can be distinguished from a region including the surrounding tissue; and a display portion that, based on the optical image formed by the optical-image forming part, displays distributions of the adipose layer and the surrounding tissue or a boundary therebetween in the optical image.

In addition, another aspect of the present invention provides a biological observation apparatus including an imaging portion that, when illumination light is radiated onto biological tissue in which surface tissue is distributed so as to cover underlying tissue, acquires a return-light image from return light from the biological tissue in a wavelength band in which an absorption characteristic of the surface tissue differs from an absorption characteristic of the underlying tissue; and a display portion that displays an image in which a distribution of tissue structure at a surface of the biological tissue is shown based on the return-light image.

The surface tissue referred to here is tissue that exists on the side that is irradiated with the illumination light, and the underlying tissue is tissue that exists on the opposite side from the side that is irradiated with the illumination light with respect to the surface tissue.

DESCRIPTION OF EMBODIMENT

A biological observation apparatus 1 according to an embodiment of the present invention will be described below with reference to the drawings.

Figure 1:
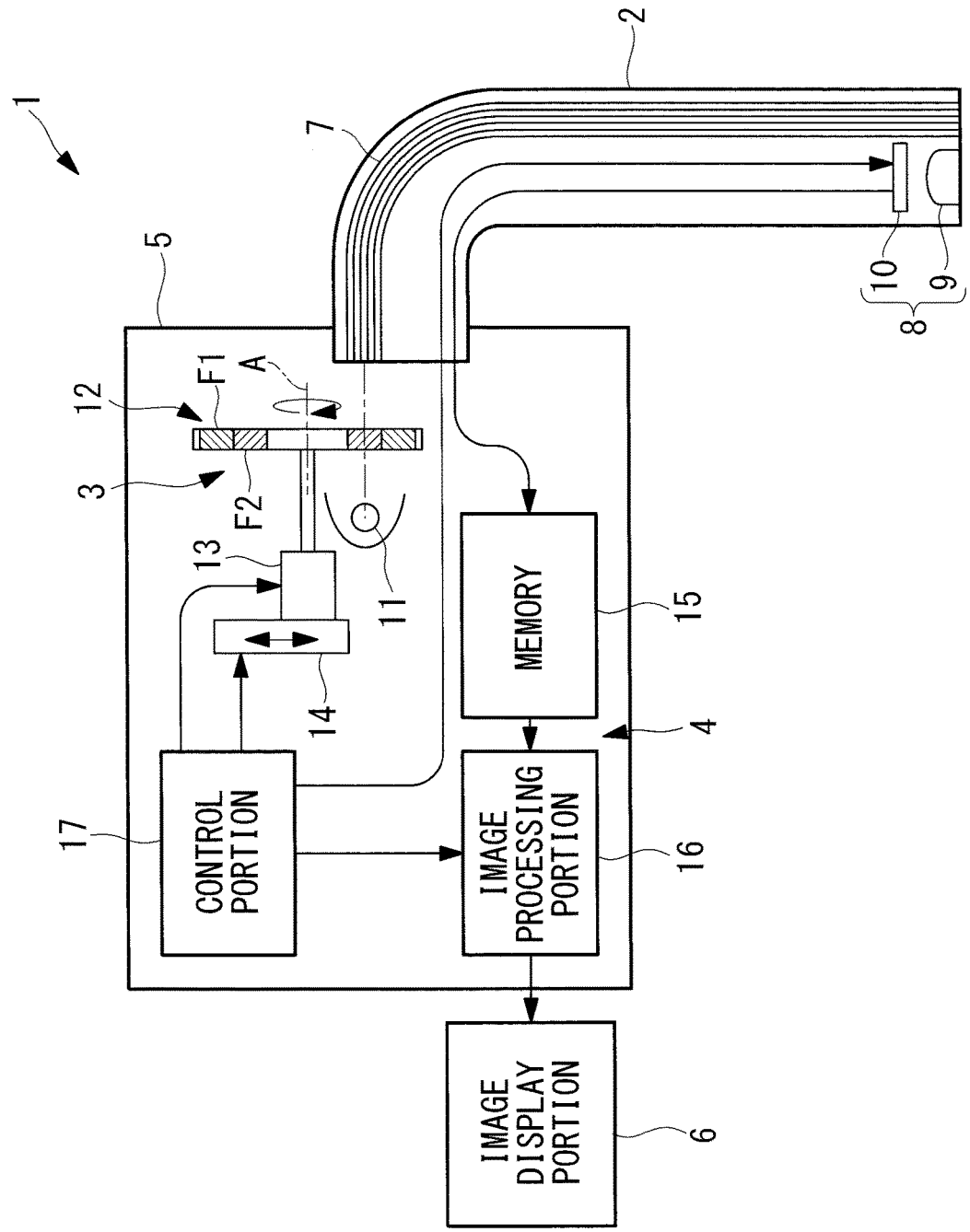
FIG. 1 is a diagram schematically showing the overall configuration of a biological observation apparatus according to an embodiment of the present invention.

First, the biological observation apparatus 1 according to this embodiment is an endoscope provided with, as shown in FIG. 1, an inserted portion 2 that is inserted into a biological subject, a main portion 5 that is connected to the inserted portion 2 and that is provided with a light source portion 3 and a signal processing portion 4, and an image display portion 6 that displays an image generated by the signal processing portion 4.

The inserted portion 2 is provided with an illumination optical system 7 that radiates light input from the light source portion 3 onto an imaging subject and an image-capturing optical system 8 that captures reflected light coming from the imaging subject. The illumination optical system 7 is a light-guide cable that is disposed over the entire length of the inserted portion 2 in the longitudinal direction thereof and that guides light that has entered from the light source portion 3 at the proximal end to the distal end.

The image-capturing optical system 8 is provided with an objective lens 9 that collects reflected light from the imaging subject due to the light radiated from the illumination optical system 7 and an imaging device 10 that captures the light collected by the objective lens 9.

The imaging device 10 is, for example, a monochrome CCD.

Figure 2:
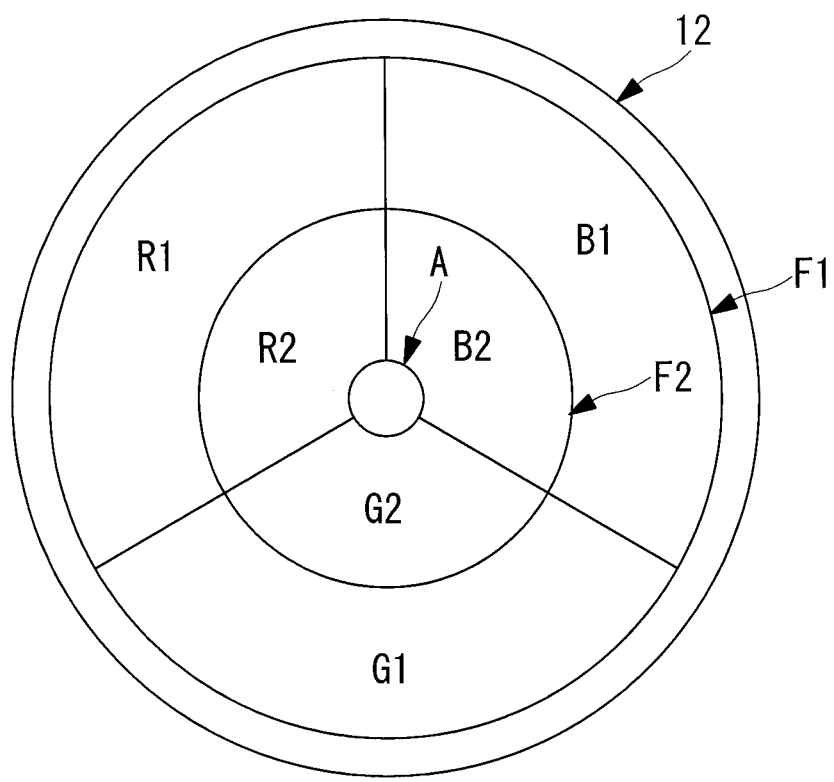
FIG. 2 is a front view showing the arrangement of individual filters in a filter turret of the biological observation apparatus in FIG. 1.

The light source portion 3 is provided with a xenon lamp 11 that emits white light in a wide wavelength band and a filter turret 12 that extracts light in a predetermined wavelength from the white light emitted from the xenon lamp 11 and that allows the light to sequentially pass therethrough in a time division manner. The filter turret 12 is provided with, for example, two types of filter groups F1 and F2 that are concentrically disposed in a radial direction centered on a rotation center A, as shown in FIG. 2. Reference sign 13 in the figure indicates a motor.

In addition, the filter turret 12 is provided so as to be movable in a direction that intersects the optical axis of the xenon lamp 11 by means of a linear motion mechanism 14. Accordingly, by placing either the filter group F1 or F2 on the optical axis of the white light from the xenon lamp 11, the filter turret 12 can allow the light selected by the filter group F1 or F2 to propagate toward the inserted portion 2.

Figure 3:
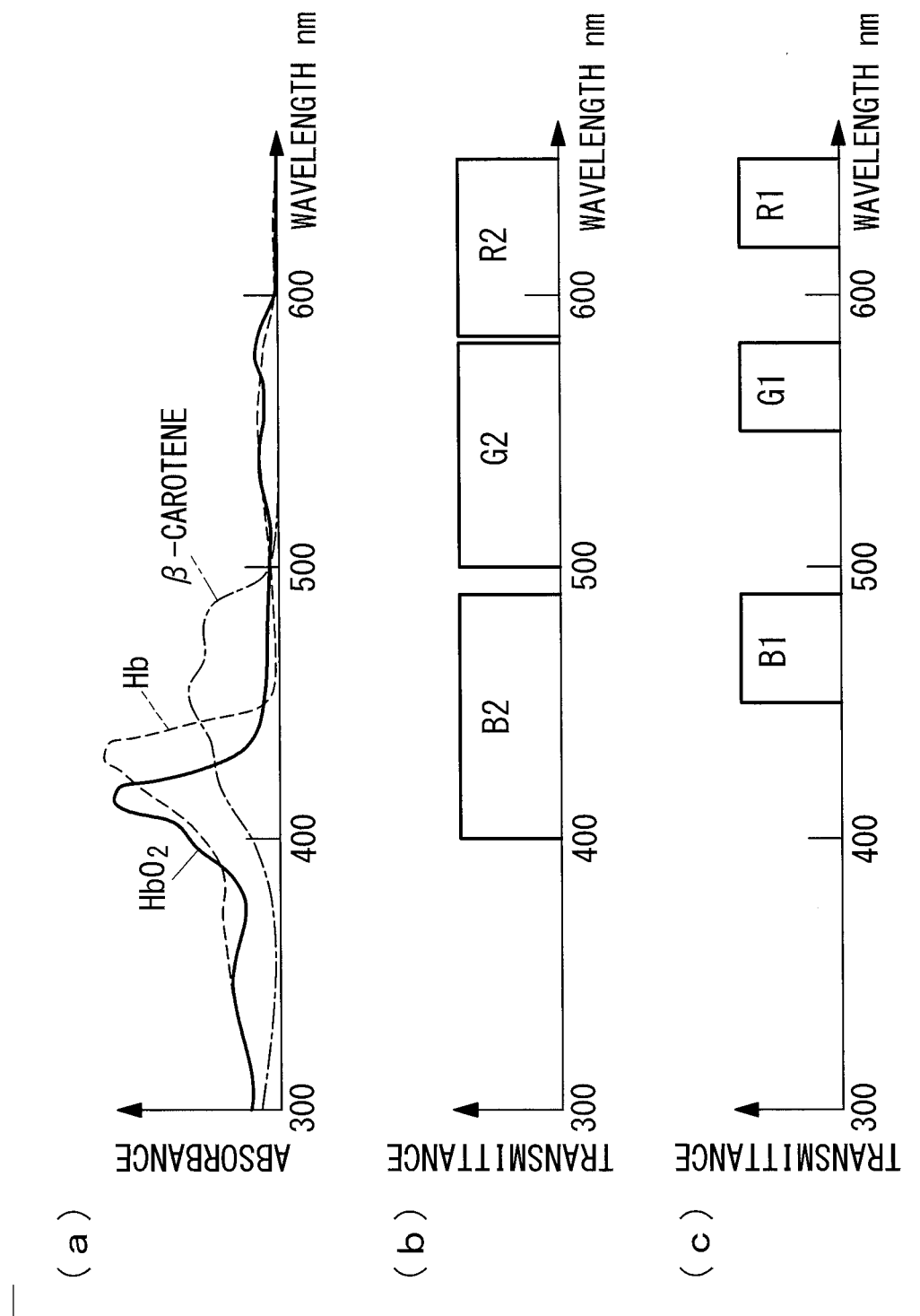
FIG. 3 is a diagram individually showing (a) an absorption characteristic of β-carotene and an absorption characteristic of hemoglobin; (b) a transmittance characteristic of the filters of the biological observation apparatus in FIG. 1, when operated in a white-light observation mode; and (c) a transmittance characteristic of the filters of the biological observation apparatus in FIG. 1, when operated in a special-light observation mode.

As shown in FIG. 3(c), the first filter group F1 is constituted of filters B1, G1, and R1 that have high transmittance for blue (B1: 450 to 480 nm), green (G1: 550 to 570 nm), and red (R1: 620 to 650 nm) in the blue, green, and red wavelength bands and that are arrayed in the circumferential direction.

As shown in FIG. 3(b), the second filter group F2 is constituted of filters B2, G2, and R2 that individually allow light in the nearly continuous wavelength bands of blue (B2: 400 to 490 nm), green (G2: 500 to 570 nm), and red (R2: 590 to 650 nm) to pass therethrough and that are arrayed in the circumferential direction.

Here, as shown in FIG. 3(a), β-carotene contained in biological tissue exhibits high absorption in the region ranging from 400 to 500 nm. In addition, hemoglobin ($HbO_2$ and Hb), which is a component in blood, exhibits high absorption in the wavelength band equal to or less than 450 nm and the wavelength band ranging from 500 to 600 nm.

In other words, because the blue wavelength band of the first filter group F1 is, as compared with the blue wavelength band of the second filter group F2, a wavelength band in which absorption by β-carotene is greater than absorption by hemoglobin, an image that is obtained by radiating this light is affected less by the absorption by the blood vessels and shows greater absorption by adipose tissue. On the other hand, a white-light image is obtained by separately capturing beams of reflected light of beams that have passed through the individual filters B2, G2, and R2 of the second filter group F2 and by combining the captured beams into an image after adding corresponding colors thereto.

In addition, because the wavelength band of the green G1 in the first filter group F1 is a region in which there is no absorption by β-carotene and absorption by hemoglobin exists, in an image obtained by radiating this light, a low intensity region indicates a region in which blood exists, for example, a blood vessel.

Furthermore, because there is no absorption either by β-carotene or by hemoglobin in the wavelength band of the red R1 in the first filter group F1, morphological features of a surface of biological tissue are shown in an image obtained by radiating this light.

The signal processing portion 4 is provided with a memory 15 that separately stores image signals acquired by the imaging device 10 depending on the wavelengths of the radiated illumination light and an image processing portion 16 that combines image signals stored in the memory 15 after adding different colors thereto. In addition, the signal processing portion 4 is provided with a control portion 17. The control portion 17 is configured so as to synchronize the timing at which the imaging device 10 captures images, rotation of the filter turret 12, and the timing at which the image processing portion 16 performs image combining processing.

In order to observe a biological subject by using the thus-configured biological observation apparatus 1 according to this embodiment, first, the second filter group F2 of the filter turret 12 is moved so as to be placed at a position on the optical axis of light from the xenon lamp 11, blue B2, green G2, and red R2 illumination light beams are sequentially radiated, and beams reflected at an imaging subject when the respective illumination light beams are radiated are sequentially captured by the imaging device 10. This observation mode is referred to as a white-light observation mode (second observation mode).

Image information corresponding to the illumination light of the respective colors is sequentially stored in the memory 15, and, at the point in time when the image information corresponding to the three types of illumination light, namely, the blue B2, green G2, and red R2, is acquired, the image processing portion 16 combines the image information. At the image processing portion 16, individual pieces of image information are assigned colors of illumination light that was radiated when the image information was captured and are combined. By doing so, a white-light image is generated, and the generated white-light image is transmitted to and displayed on the image display portion 6.

In the white-light image, for example, the blood vessels are displayed in red because absorption occurs in the blue B2 and green G2 wavelength bands in a region in which the blood vessels exist. In addition, adipose tissue is displayed in yellow because the blue B2 is absorbed in a region in which adipose tissue exists. However, when the adipose tissue is extremely thin, the color of blood vessels in an organ behind the adipose tissue passes therethrough, thus making it difficult to ascertain the existence of the adipose tissue.

Therefore, in such a case, the first filter group F1 of the filter turret 12 is moved so as to be placed at a position on the optical axis of light from the xenon lamp 11, the blue B1, green G1, and red R1 illumination light beams are sequentially radiated, and beams reflected at the imaging subject when the respective illumination light beams are radiated are sequentially captured by the imaging device 10. This observation mode is referred to as a special-light observation mode (first observation mode).

Then, in the same manner as when capturing a white-light image, image information corresponding to the illumination light of the respective colors is sequentially stored in the memory 15, and, at the point in time when the image information corresponding to the three types of illumination light, namely, blue B1, green G1, and red R1, is acquired, the image processing portion 16 combines the image information. At the image processing portion 16, individual pieces of image information are assigned colors of illumination light that was radiated when the image information was captured and are combined.

In this case, with this embodiment, the wavelength band of blue B1 in this special-light observation mode is a wavelength band in which the absorption by β-carotene is greater than the absorption by hemoglobin, as compared with the wavelength band of blue B2. Therefore, an image that is obtained by radiating the light in this wavelength band is affected less by the absorption by blood and is affected more by the absorption by adipose tissue, as compared with an image obtained by radiating the blue light B2; in other words, it is possible to obtain an image that better shows the distribution of adipose tissue.

In addition, the wavelength band of green G1 is a wavelength band in which there is no absorption by β-carotene and the absorption by hemoglobin is high. Therefore, in an image obtained by radiating light in this wavelength band, it can be assumed that a low luminance region indicates a region in which blood exists regardless of the presence of adipose tissue. In other words, it is possible to clearly display tissue containing a large amount of hemoglobin, such as blood, blood vessels, and so forth.

Furthermore, the wavelength band of red R1 is a wavelength band in which neither β-carotene nor hemoglobin exhibit absorption. Therefore, it can be assumed that an image obtained by radiating light in this wavelength band indicates a luminance distribution based on morphological features at a surface of a biological subject.

Therefore, an image obtained by combining these images after adding different colors thereto is an image in which the presence of adipose tissue, the presence of blood vessels, and morphological features at the surface of the biological subject all are displayed by using different colors.

In other words, in an image acquired in the special-light observation mode, it is possible to more clearly display adipose tissue even if the adipose tissue is extremely thin and an organ with a large amount of blood exists behind the adipose tissue.

As a result, there is an advantage in that, for example, when removing a target organ, as in prostate removal or rectectomy, it is possible to clearly observe the boundary between the target organ and the adipose tissue that is distributed around the target organ, and that it is possible to perform surgery while avoiding damage to peripheral nerves that exist in the adipose tissue, which appear white or transparent, and have diameters of 50 to 300 μm.

Figure 10:
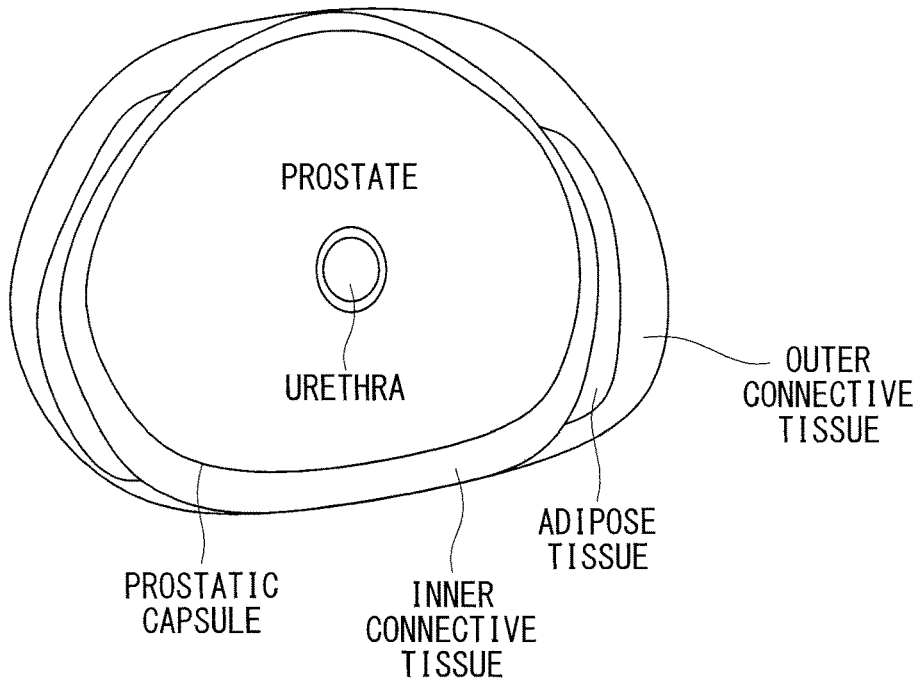
FIG. 10 is a diagram showing, as an example of biological tissue to which the present invention is applied, cross-sections of a prostate and connective surrounding tissue thereof.

For example, in the case in which the target organ is the prostate, connective tissue is distributed around the prostate, as shown in FIG. 10, and the connective tissue contains adipose tissue (adipose layer), inner connective tissue that is located on the prostate side of the adipose tissue, and outer connective tissue that covers the surface of the adipose tissue. Thus, among the individual tissues that constitute the connective tissue, the adipose tissue contains a greater number of nerves as compared with the connective tissue other than the adipose tissue, as shown in FIG. 11.

Figure 11:
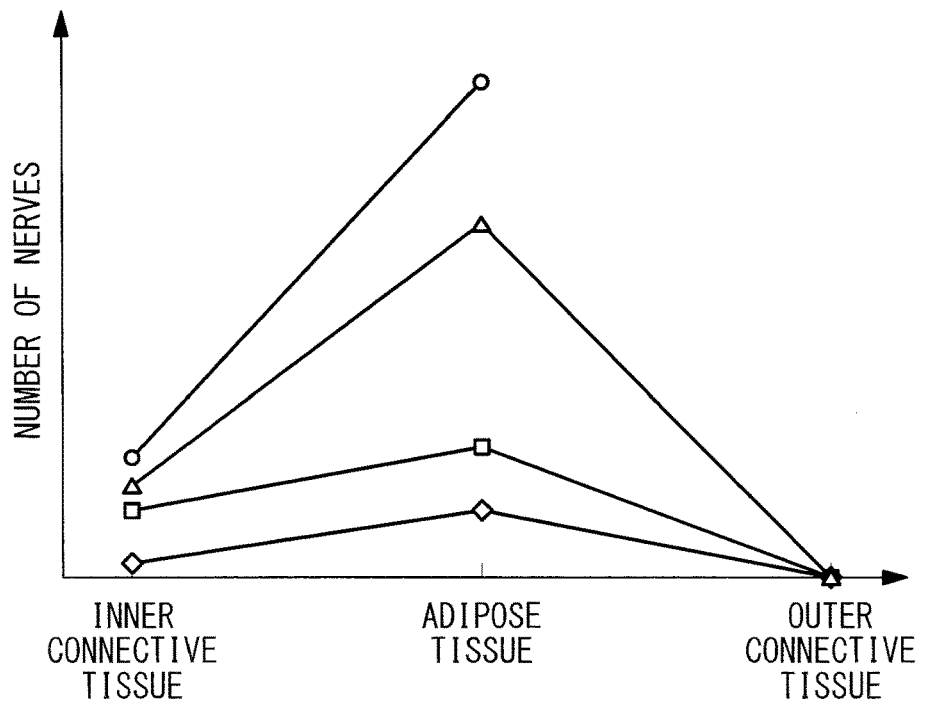
FIG. 11 is a graph showing the relationships between the number of nerves and connective tissue and adipose tissue.

FIG. 11 is a graph showing, for four samples, the relationships between the number of nerves and the connective tissue and the adipose tissue.

In this way, the adipose tissue serves as an indicator for the presence of nerves. Such an indicator is referred to as a merkmal and serves to make a distinction between tissues in an actual biological subject.

In this embodiment, a description has been given of an embodiment in which, among optical characteristics, a spectral characteristic is used.

Thus, with the biological observation apparatus according to this embodiment, by utilizing differences in optical characteristics between an adipose layer and surrounding tissue, it is possible to form an optical image in which a region including an adipose layer that contains a greater number of nerves relative to the surrounding tissue can be distinguished from a region including the surrounding tissue.

Figure 12:
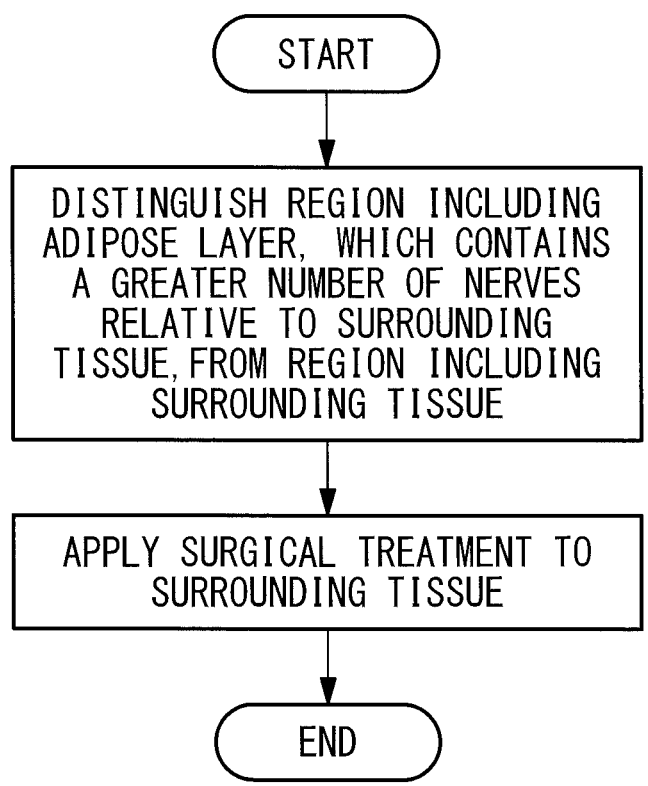
FIG. 12 is a flowchart showing a method for applying surgical treatment while preserving nerves that exist around a target organ.

In addition, a method according to this embodiment in which surgical treatment is applied in order to remove a target organ while preserving nerves that exist around the target organ includes a step of distinguishing, in a specific portion, a region including an adipose layer that contains a greater number of nerves relative to surrounding tissue from a region including the surrounding tissue and a step of applying surgical treatment to the surrounding tissue. FIG. 12 is a flow chart showing a method of applying surgical treatment while preserving nerves that exist around a target organ.

Here, a method of applying surgical treatment while preserving nerves that exist around a target organ, when, for example, the target organ is the prostate will be described.

Membranes on the outer side of the prostate (surrounding tissue) have a structure including, from the portion closer to the prostate, the prostatic capsule, the prostatic fascia (inner connective tissue), the outer pelvic fascia (outer connective tissue), and the inner pelvic fascia. As compared with the surrounding tissue, nerves more often run in adipose tissue (adipose layer) that exists inside the outer pelvic fascia. Because of this, in order to remove the prostate while preserving the nerves that surround the prostate, the prostate and the adipose tissue are separated so as not to remove the adipose tissue.

In the procedure for removing the prostate, first, a space is created in front of the urinary bladder and the prostate, and tissue existing in front of the urinary bladder and the prostate is removed. The urinary bladder and the prostate are subsequently sectioned, the vas deferens is cut, and the seminal vesicle is separated. Then, the prostate and the adipose tissue are subsequently separated at the surrounding tissue that exists therebetween (inside the prostatic fascia).

To perform separation inside the prostatic fascia, the prostatic capsule and the prostatic fascia are separated by using forceps or the like from the sectioned surface between the urinary bladder and the prostate, thus exposing the prostatic capsule. The prostatic capsule and the prostatic fascia are bluntly separated, as they are, all the way to the apex of the prostate.

However, because the prostatic fascia has an intricate multilayer membrane structure that is partially fused, it is difficult to perform separation all the way to the apex while appropriately holding the separated surfaces. In the case in which the separated surfaces are displaced toward the outer pelvic fascia where the adipose tissue exists, it becomes more likely for nerves existing inside the adipose tissue to be damaged. However, it is unlikely for nerves to be damaged even if the separated surfaces are displaced toward the adipose tissue, unless the adipose tissue is exposed at the separated surfaces.

Accordingly, the surrounding tissue that exists between the prostate and the adipose tissue is separated so as not to cut into the adipose tissue while repeating the process of distinguishing regions including adipose tissue that contains a greater number of nerves relative to the surrounding tissue from regions including the surrounding tissue, and the process of separating the prostatic fascia that exists in the region between the prostate and the adipose tissue. In actual practice, the biological observation apparatus according to this embodiment is employed to make the distinction.

By making distinction in this way, in the case in which the separated surfaces are displaced toward the adipose tissue, specifically, in the case in which the adipose tissue is exposed at the separated surface or in the case in which, at the separated surface on the side where adipose tissue exists, surrounding tissue at an adipose tissue surface is thin and the adipose tissue can be observed through the surrounding tissue, the separation can be performed at a position at which nerves are less likely to be damaged by correcting the separated surface to the prostate side from the adipose tissue side.

Figure 4:
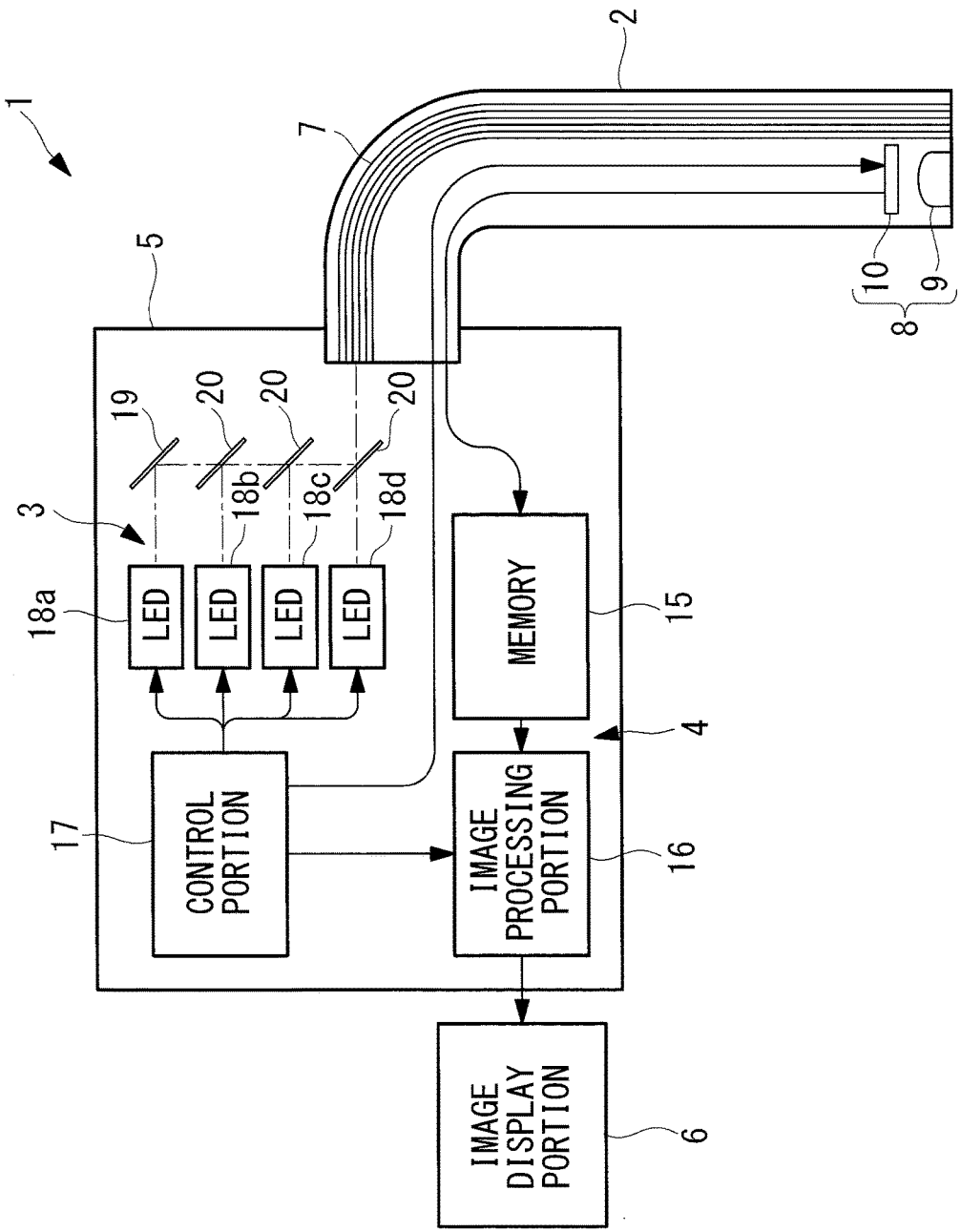
FIG. 4 is a diagram schematically showing the overall configuration of a first modification of the biological observation apparatus in FIG. 1.

In this embodiment, the light source portion 3 sequentially emits light in different wavelength bands by means of the xenon lamp 11 and the filter turret 12; alternatively, as shown in FIG. 4, a plurality of light emitting diodes (LEDs) 18a to 18d that emit light in different wavelength bands may be disposed, and the light therefrom may be made to enter the same light-guide cable 7 by means of a mirror 19 and dichroic mirrors 20.

Figure 5:
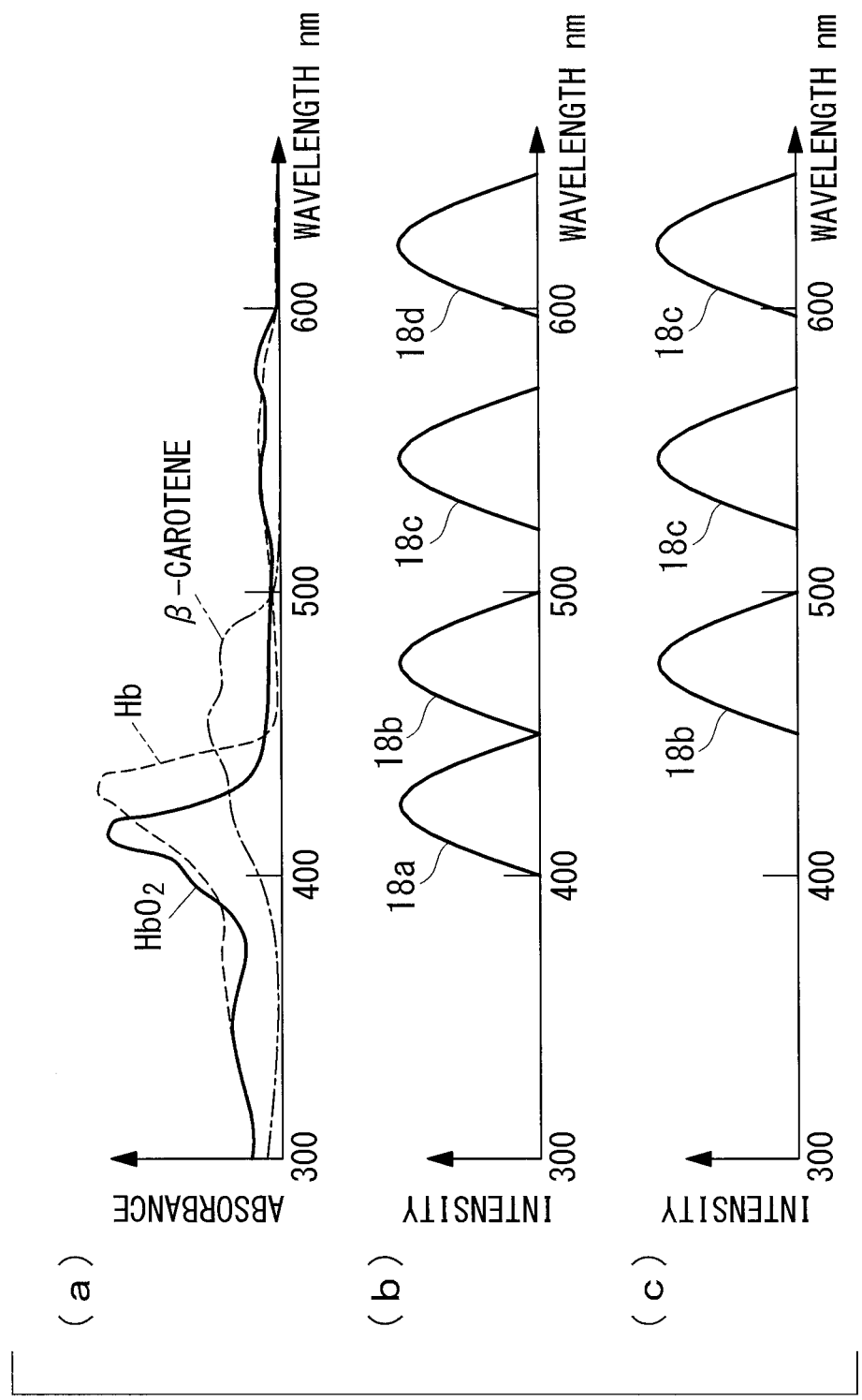
FIG. 5 is a diagram individually showing (a) an absorption characteristic of β-carotene and an absorption characteristic of hemoglobin; (b) a light intensity characteristic of LEDs used in the white-light observation mode of the biological observation apparatus in FIG. 4; and (c) a light intensity characteristic of LEDs used in the special-light observation mode of the biological observation apparatus in FIG. 4.

The example shown in FIG. 4 is provided with four light emitting diodes 18a to 18d for wavelength bands ranging from 400 to 450 nm, 450 to 500 nm, 520 to 570 nm, and 600 to 650 nm. Thus, in the white-light observation mode, as shown in FIG. 5(c), light from the light emitting diodes 18a and 18b, ranging from 400 to 500 nm, is used as blue illumination light, light from the light emitting diode 18c, ranging from 520 to 570 nm, is used as green illumination light, and light from the light emitting diode 18d, ranging from 600 to 650 nm, is used as red illumination light. On the other hand, in the special-light observation mode, as shown in FIG. 5(b), the light emitting diode 18b for the range from 450 to 500 nm is used for blue illumination light.

As a result, as with the biological observation apparatus 1 in FIG. 1, thin adipose tissue that exists at a surface of an organ can also be displayed so as to stand out in the special-light observation mode. FIG. 5(a) is the same as FIG. 3(a).

Figure 6:
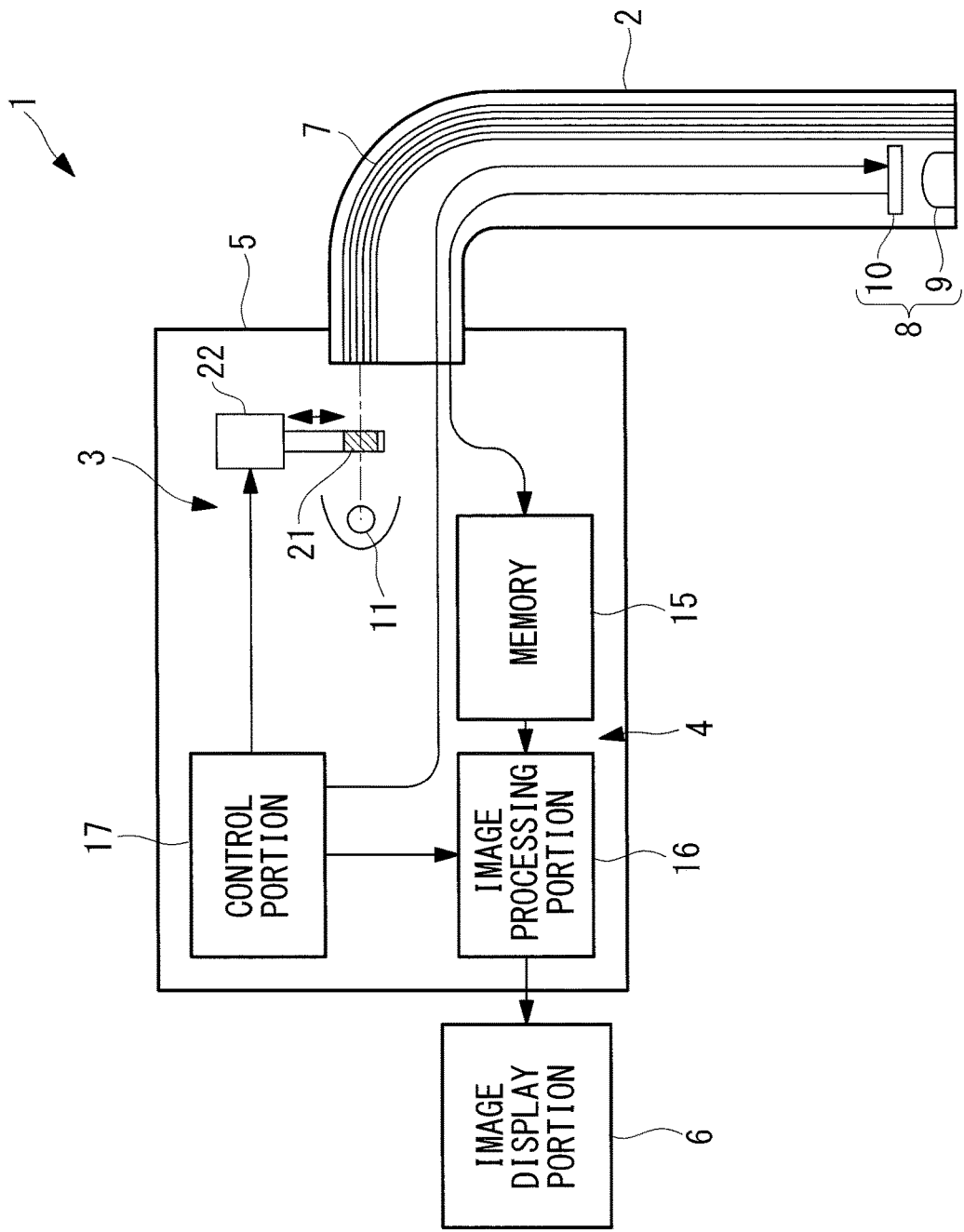
FIG. 6 is a diagram schematically showing the overall configuration of a second modification of the biological observation apparatus in FIG. 1.

In addition, as shown in FIG. 6, a color CCD may be used as the imaging device 10, instead of a monochrome CCD, and a short-wavelength cut filter 21 that can be placed on and retracted from the optical axis of light from the xenon lamp 11 may be provided instead of the filter turret 12. In the figure, reference sign 22 indicates a linear motion mechanism that is controlled by the control portion 17 to place/retract the short-wavelength cut filter 21 on/from the optical axis.

Figure 7:
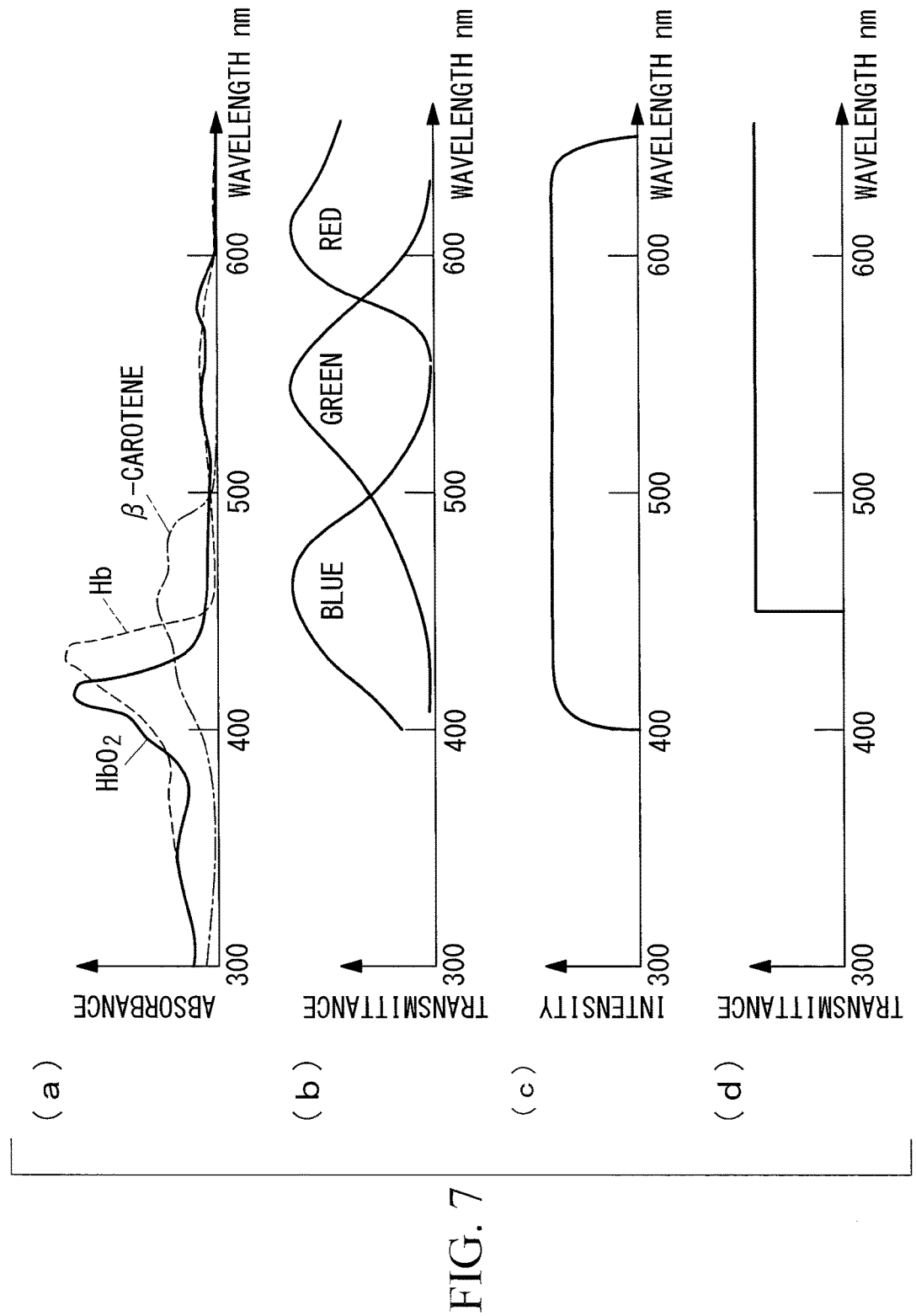
FIG. 7 is a diagram individually showing (a) an absorption characteristic of β-carotene and an absorption characteristic of hemoglobin; (b) a transmittance characteristic of color filters provided in a color CCD of the biological observation apparatus in FIG. 6; (c) a light intensity characteristic of a xenon lamp of the biological observation apparatus in FIG. 6; and (d) a transmittance characteristic of a filter of the biological observation apparatus in FIG. 6, when operated in the special-light observation mode.

As shown in FIG. 7(d), the short-wavelength cut filter 21 is configured so as to block light in wavelength bands less than 450 nm and allows light in wavelength bands equal to or greater than 450 nm to pass therethrough.

As shown in FIG. 7(b), the imaging device 10 is provided with color filters (not shown) that exhibit transmittance for each color.

In addition, the xenon lamp 11 has an intensity spectrum such as the one shown in FIG. 7(c). FIG. 7(a) is the same as FIG. 3(a).

The short-wavelength cut filter 21 is retracted from the optical axis in the white-light observation mode, and, the short-wavelength cut filter 21 is placed on the optical axis in the special-light observation mode. Then, images acquired based on pixels in the imaging device 10 that correspond to individual colors are separately stored in the memory 15 and are combined at the image processing portion 16. By doing so, as with the biological observation apparatus 1 in FIG. 1, thin adipose tissue that exists at a surface of an organ can also be displayed so as to stand out in the special-light observation mode.

Figure 8:
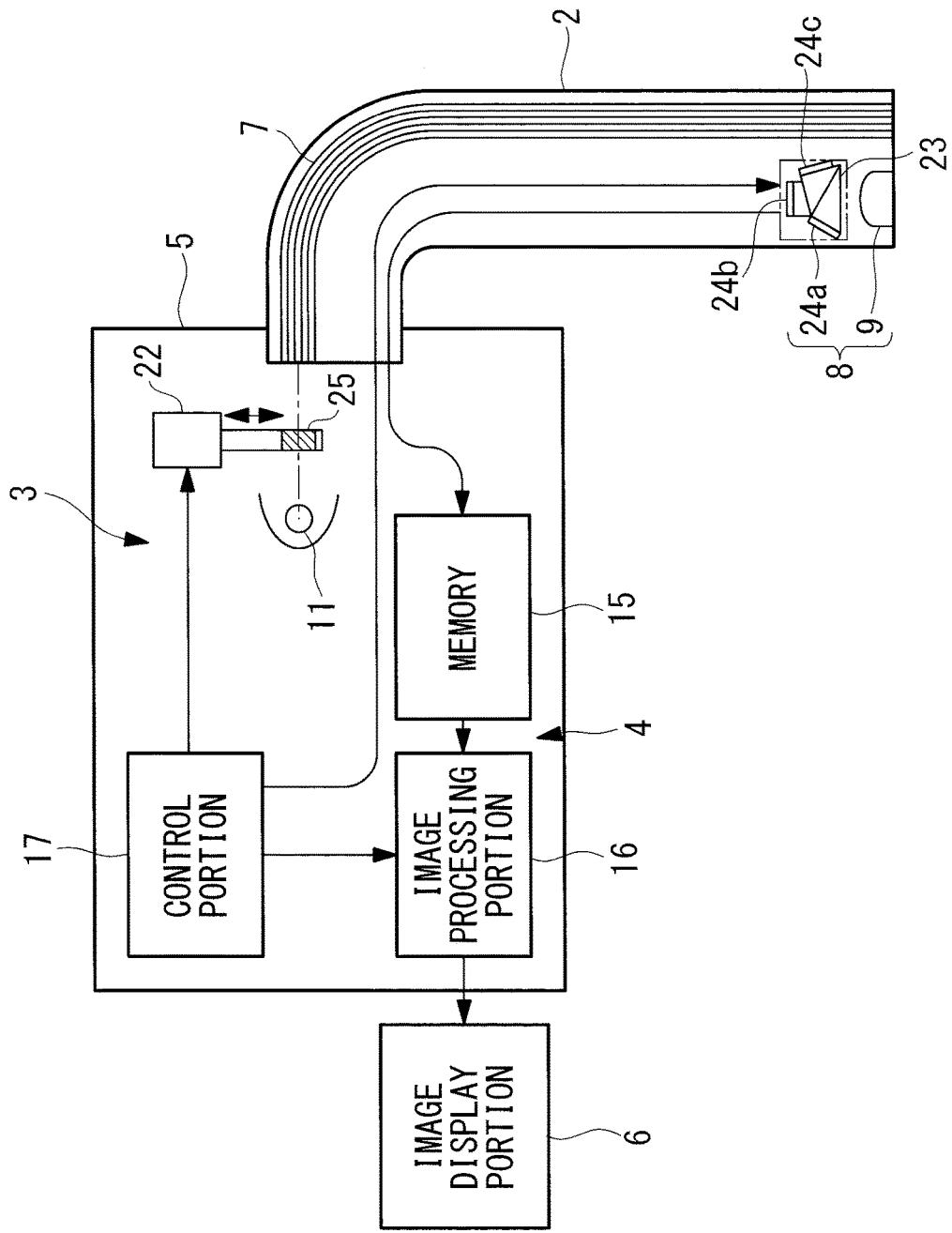
FIG. 8 is a diagram schematically showing the overall configuration of a third modification of the biological observation apparatus in FIG. 1.

Furthermore, as shown in FIG. 8, it is permissible to employ a 3-CCD system that is provided with a color-separation prism 23 that separates reflected light returning from an imaging subject depending on wavelength bands and three monochrome CCDs 24a to 24c that capture light in the respective wavelength bands.

Figure 9:
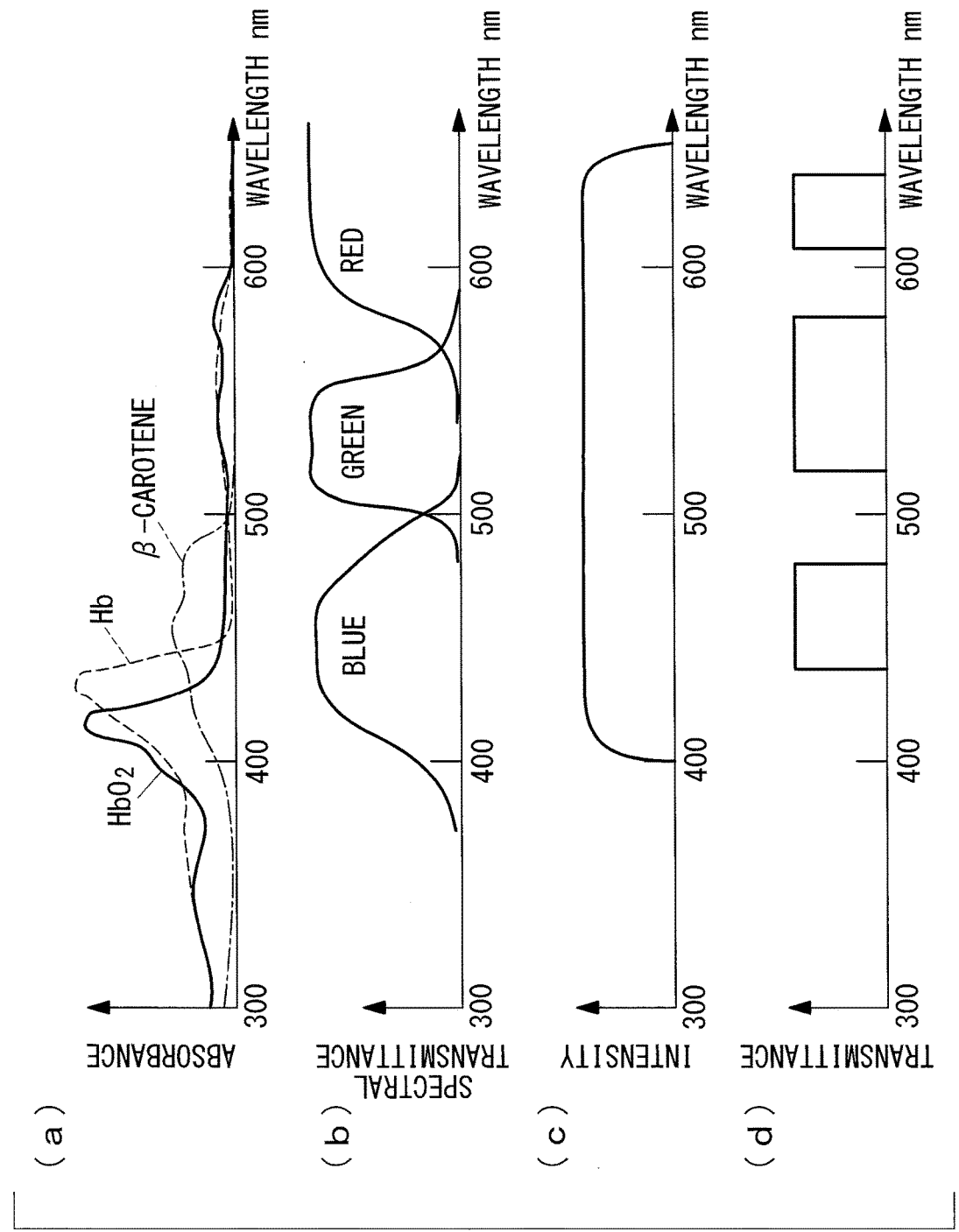
FIG. 9 is a diagram individually showing (a) an absorption characteristic of β-carotene and an absorption characteristic of hemoglobin; (b) a spectral transmittance characteristic of a color-separation prism of the biological observation apparatus in FIG. 8; (c) a light intensity characteristic of a xenon lamp of the biological observation apparatus in FIG. 8; and (d) a transmittance characteristic of a filter of the biological observation apparatus in FIG. 8, when operated in the special-light observation mode.

The color-separation prism 23 is configured so as to spectrally separate reflected light from an imaging subject depending on wavelength bands in accordance with transmittance characteristic shown in FIG. 9(b).

FIG. 9(a) is the same as FIG. 3(a). Also, FIG. 9(c) is the same as FIG. 7(c).

In this case also, a filter 25 that can be placed on and retracted from the optical axis of the light from the xenon lamp 11 by the linear motion mechanism 22 should be provided instead of the filter turret 12. As shown in FIG. 9(d), the filter 25 is configured so as to allow light in three desired wavelength bands to pass therethrough and blocks light in other wavelength bands.

Also, the filter 25 is retracted from the optical axis in the white-light observation mode, and the filter 25 is placed on the optical axis in the special-light observation mode. Then, images acquired by the individual monochrome CCDs 24a to 24c are separately stored in the memory 15 and are combined at the image processing portion 16. By doing so, as with the biological observation apparatus 1 in FIG. 1, thin adipose tissue that exists at a surface of an organ or other tissue, such as connective tissue or the like, can also be displayed so as to stand out in the special-light observation mode.

In addition, in this embodiment, a magnification switching portion (not shown) that switches the observation magnification may be provided, and the observation mode may be switched to the special-light observation mode when the observation magnification is switched to a high magnification and to the white-light observation mode when the observation magnification is switched to a low magnification.

By using the special-light observation mode during high magnification observation, it is possible to perform precise treatment while checking the boundary between adipose tissue and other tissue, and, by using the white-light observation mode during low-magnification observation, it is possible to roughly observe the entire portion to be treated.

In addition, in this embodiment, observation is performed by spectrally separating reflected light from an imaging subject due to light from the illumination optical system 7; alternatively, the following types of observation may be performed.

(A) to (F) are types of observation in which adipose tissue and connective tissue other than the adipose tissue are distinguished from each other by using differences in optical characteristics other than a spectral characteristic.

(A) Auto-fluorescence: although adipose tissue exhibits low auto-fluorescence, because connective tissue other than adipose tissue contains a large amount of collagen, which is an auto-fluorescent substance, auto-fluorescence thereof is high, and it is possible to make a distinction between the two by using this difference.

(B) Polarization: by using differences in polarization characteristics, such as depolarization ratio, polarization ratio, phase difference, and so forth, between adipose tissue and connective tissue other than the adipose tissue, it is possible to make a distinction between the two.

(C) Raman scattering: by using differences between molecules that constitute adipose tissue and molecules that constitute connective tissue other than the adipose tissue, it is possible to make a distinction between the two.

(D) Infrared light: because adipose tissue contains less water than connective tissue other than the adipose tissue, absorption of infrared light is low. It is possible to make a distinction between the two by using this difference in infrared absorption.

(E) Staining: staining is performed by using a dye that tends to accumulate in adipose tissue. The adipose tissue takes up dye having high adipose tissue solubility. By using differences in optical characteristics due to a difference in the accumulation levels of the dye, it is possible to make a distinction between adipose tissue and connective tissue other than adipose tissue.

(F) OCT: an image is formed by using a difference in refractive index between adipose tissue and connective tissue other than the adipose tissue. It is possible to make a distinction between the two by using the difference in refractive index.

(G) Image processing: by processing an image acquired by capturing return light from an imaging subject by optical-image forming part by using, for example, spectral estimation, an optical image of a predetermined wavelength band is formed, and it is possible to make a distinction between adipose tissue and connective tissue other than the adipose tissue based on this optical image.

In addition, as will be described in (H) and (I), it is possible to use a characteristic other than an optical characteristic so long as adipose tissue and connective tissue other than adipose tissue can be distinguished from each other. It is also possible to make a distinction between the two by using such a characteristic and the optical characteristic in combination.

(H) Ultrasonic waves: by forming a tomographic image by using a difference in acoustic impedance between adipose tissue and connective tissue other than the adipose tissue, it is possible to make a distinction between the two.

(I) MRI: by forming an image in which adipose tissue and connective tissue other than the adipose tissue are distinguished from each other by using nuclear magnetic resonance phenomena, it is possible to make a distinction between the two.

According to the above embodiment, following aspects can be introduced.

An aspect of the present invention provides a biological observation apparatus for performing surgical treatment, including an optical-image forming part for forming an optical image in which, by using a difference in an optical characteristic between an adipose layer and surrounding tissue of the adipose layer in a specific portion, a region including the adipose layer, which contains a greater number of nerves relative to the surrounding tissue, can be distinguished from a region including the surrounding tissue; and a display portion that, based on the optical image formed by the optical-image forming part, displays distributions of the adipose layer and the surrounding tissue or a boundary therebetween in the optical image.

In the above-described aspect, the optical characteristic may be a spectral characteristic.

In addition, in the above-described aspect, the optical-image forming part may be provided with an irradiating portion that radiates illumination light onto a biological tissue and an imaging portion that, of reflected light reflected at the biological tissue due to the illumination light radiated by the irradiating portion, captures reflected light in a wavelength band in which an absorption characteristic of β-carotene is greater than an absorption characteristic of hemoglobin, thus acquiring a reflected-light image.

With this aspect, illumination light is radiated onto biological tissue from the irradiating portion, reflected light reflected at the biological tissue is captured by the imaging portion, and thus, a reflected-light image is acquired. Because the imaging portion captures reflected light in a wavelength band in which the absorption characteristic of β-carotene is greater than the absorption characteristic of hemoglobin, it is possible to acquire a reflected-light image that is affected less by the presence of blood vessel and is affected more by the presence of adipose tissue.

The inventors have focused on the fact that a target organ such as the prostate is covered with a thin adipose layer and nerves surrounding the target organ exist inside the adipose layer. With white-light observation, adipose tissue appears yellow as a whole because adipose tissue tends to absorb blue light. In addition, blood appears red as a whole because blood absorbs blue light and green light. In other words, blue light is absorbed both by adipose tissue and blood. Also, because an adipose layer that covers a target organ is thin, the adipose layer tends to be affected by underlying tissue.

Therefore, by performing observation by displaying on the display portion the reflected-light image, which is acquired by capturing reflected light in a wavelength band in which the absorption characteristic of β-carotene contained in adipose tissue is greater than the absorption characteristic of hemoglobin contained in blood, it is possible to easily judge that a portion in the reflected-light image whose luminance in the wavelength band in question is low does not indicate other underlying tissue that contains a large amount of blood but indicates a thin adipose layer that covers the target organ. In other words, in the case of rectectomy, prostatectomy, and so forth, it is possible to make it easier to recognize adipose tissue in a reflected-light image being used for observation, and it is possible to perform surgery so as not to damage nerves distributed in an adipose layer.

In the above-described aspect, the imaging portion may capture reflected light in a wavelength band within a range from 450 to 500 nm.

In addition, in the above-described aspect, the imaging portion may acquire a first reflected-light image and a second reflected-light image by capturing first reflected light based only on a first wavelength band within a range from 450 to 500 nm, where the absorption characteristic of β-carotene is greater than the absorption characteristic of hemoglobin, and second reflected light based only on a second wavelength band within a range from 500 to 600 nm, where the absorption characteristic of hemoglobin is greater than the absorption characteristic of β-carotene, by making a distinction between the two, and the display portion may display a combined image formed by combining the first reflected-light image and the second reflected-light image by using different colors.

By doing so, a region in which adipose tissue exists can be made clear by using the first reflected-light image, and a region in which blood vessels exist can be made clear by using the second reflected-light image. Then, by combining the two images by using different colors, it is possible to display an image by making a distinction between adipose tissue and other tissue.

In addition, in the above-described aspect, the imaging portion may acquire a third reflected-light image by capturing third reflected light based only on a third wavelength band within a range from 600 to 650 nm, where the absorption characteristic of β-carotene and the absorption characteristic of hemoglobin are both low, by making a distinction from the first reflected-light image and the second reflected-light image, and the display portion may display a combined image formed by combining the first reflected-light image, the second reflected-light image, and the third reflected-light image by using different colors.

By doing so, because the third reflected-light image shows the shape of a surface of biological tissue, which is not affected either by β-carotene or by hemoglobin, by combining the third reflected-light image with the first and second reflected-light images and by using a different color when displaying them, visually observed biological tissue can easily be associated with the biological tissue in the image displayed on the display portion.

In addition, in the above-described aspect, the irradiating portion may radiate illumination light based only on a wavelength band in which the absorption characteristic of β-carotene is greater than the absorption characteristic of hemoglobin.

By doing so, reflected light reflected at the biological tissue becomes reflected light based only on the wavelength band in which the absorption characteristic of β-carotene is greater than the absorption characteristic of hemoglobin, and therefore, it is possible to suppress the influence of blood vessels and to easily acquire reflected light that is mainly affected by adipose tissue.

In addition, in the above-described aspect, the irradiating portion may separately radiate first illumination light based only on the first wavelength band and second illumination light based only on the second wavelength band.

By doing so, it is possible to easily and separately acquire the first reflected-light image, displaying adipose tissue, and the second reflected-light image, displaying blood.

In addition, in the above-described aspect, the irradiating portion may separately radiate first illumination light based only on the first wavelength band, second illumination light based only on the second wavelength band, and third illumination light based only on the third wavelength band.

By doing so, it is possible to easily and separately acquire the first reflected-light image, displaying adipose tissue, the second reflected-light image, displaying blood, and the third reflected-light image, displaying the shape of the biological tissue.

In addition, in the above-described aspect, the irradiating portion may radiate illumination light in wavelength bands including the first wavelength band to the third wavelength band at the same time, and the imaging portion may be provided with a color CCD.

By doing so, by radiating illumination light in a wide band ranging from the first wavelength band to the third wavelength band, reflected light in the first wavelength band, reflected light in the second wavelength band, and reflected light in the third wavelength band that return from the biological tissue can be separately detected by the color CCD of the imaging portion, and it is possible to easily and separately acquire the first to third reflected-light images.

In addition, in the above-described aspect, the irradiating portion may radiate illumination light in wavelength bands including from the first wavelength band to the third wavelength band at the same time, and the imaging portion may be provided with a spectroscopic part for spectrally separating reflected light from the biological tissue into reflected light in a first wavelength band, a second wavelength band, and a third wavelength band and three imaging devices that separately capture the reflected light in the first to third wavelength bands spectrally separated by the spectroscopic part.

By doing so, by radiating illumination light in a wide band ranging from the first wavelength band to the third wavelength band, reflected light in the first wavelength band, reflected light in the second wavelength band, and reflected light in the third wavelength band that return from the biological tissue are spectrally separated by the spectroscopic part and are separately captured by the three imaging devices, thus making it possible to easily and separately acquire the first to third reflected-light images.

In addition, the above-described aspect may be provided with a mode switching portion that can switch between a first observation mode for capturing reflected light based only on a wavelength band in which, in a blue wavelength band, the absorption characteristic of β-carotene is greater than the absorption characteristic of hemoglobin and a second observation mode for capturing reflected light in all wavelength bands from blue to red.

By doing so, by switching to the second observation mode by means of the mode switching portion, it is possible to perform observation in which a combined image obtained by capturing reflected light in all wavelength bands, as with the case of visual observation, is displayed, and, by switching to the first observation mode, it is possible to perform observation in which adipose tissue is made easier to view.

In addition, the above-described aspect may be provided with a magnification switching portion that can switch an observation magnification, wherein the mode switching portion may switch to the first observation mode when the magnification switching portion switches the observation magnification to a high magnification and to the second observation mode when the magnification switching portion switches the observation magnification to a low magnification.

By doing so, when performing low-magnification observation over a large area by setting the observation magnification to a low magnification by means of the magnification switching portion, by switching to the second observation mode by means of the mode switching portion, it is possible to perform observation in which a combined image obtained by capturing reflected light in all wavelength bands, as with the case of visual observation, is displayed, and, when the observation magnification is switched to a high magnification by means of the magnification switching portion, by switching to the first observation mode by means of the mode switching portion, it is possible to perform observation in which adipose tissue is made easier to view.

In addition, another aspect of the present invention provides a biological observation apparatus including an imaging portion that, when illumination light is radiated onto biological tissue in which surface tissue is distributed so as to cover underlying tissue, acquires a return-light image from return light from the biological tissue in a wavelength band in which an absorption characteristic of the surface tissue differs from an absorption characteristic of the underlying tissue; and a display portion that displays an image in which a distribution of tissue structure at a surface of the biological tissue is shown based on the return-light image.

The surface tissue referred to here is tissue that exists on the side that is irradiated with the illumination light, and the underlying tissue is tissue that exists on the opposite side from the side that is irradiated with the illumination light with respect to the surface tissue.

In the above-described aspect, the imaging portion may acquire a return-light image in a wavelength band in which the absorption characteristic of the surface tissue is greater than the absorption characteristic of the underlying tissue.

In this case, because radiated light is mainly absorbed by the surface tissue, there is a greater amount of return light from a region in which the surface tissue is thin, and there is less return light from a region in which the surface tissue is thick. Due to this effect, it is possible to obtain an image that shows the difference in the thickness of the surface tissue.

In addition, in the above-described aspect, the imaging portion may acquire a return-light image in a wavelength band in which the absorption characteristic of the surface tissue is less than the absorption characteristic of the underlying tissue.

In this case, because the radiated light is mainly absorbed by the underlying tissue, there is less return light from a region in which the surface tissue is thin, and there is a greater amount of return light from a region in which the surface tissue is thick. Due to this effect, it is possible to obtain an image that shows the difference in the thickness of the surface tissue.

In addition, in the above-described aspect, the display portion may display an image in which a distribution of the surface tissue is shown based on the return-light image.

In addition, in the above-described aspect, the display portion may display an image in which a distribution of the underlying tissue is shown based on the return-light image.

In addition, in the above-described aspect, one of the surface tissue and the underlying tissue may be an adipose layer containing a nerve.

In addition, in the above-described aspect, the absorption characteristic of the surface tissue may be the absorption characteristic of β-carotene.

In addition, in the above-described aspect, the absorption characteristic of the surface tissue may be the absorption characteristic of hemoglobin.

In addition, in the above-described aspect, the wavelength band may be a wavelength band in which the absorption characteristic of β-carotene is greater than the absorption characteristic of hemoglobin.

In addition, in the above-described aspect, the wavelength band may be in a range from 450 to 500 nm.

In addition, in the above-described aspect, the wavelength band may be a wavelength band in which the absorption characteristic of β-carotene is less than the absorption characteristic of hemoglobin.

In addition, in the above-described aspect, the wavelength band may be in a range from 500 to 600 nm.

In addition, in the above-described aspect, the return light may be reflected light.

REFERENCE SIGNS LIST 1 biological observation apparatus
3 light source portion (irradiating portion)
6 image display portion (display portion)
7 light-guide cable (irradiating portion)
8 image-capturing optical system (imaging portion)
10 imaging device (color CCD)
17 control portion (mode switching portion)
23 color-separation prism (spectroscopic part)
24a to 24c monochrome CCD (imaging device)

The invention claimed is:

1. A biological observation apparatus, comprising:
an optical-image forming part for forming an optical image in which, by using a difference in an optical characteristic between an adipose layer and surrounding tissue of the adipose layer in a specific portion, a region including the adipose layer, which contains a greater number of nerves relative to the surrounding tissue, can be distinguished from a region including the surrounding tissue, wherein the optical-image forming part comprises a light source that is configured to radiate illumination light onto a biological tissue at a plurality of different, predetermined wavelengths and a light guide configured to transmit light from the light source to the biological tissue; and
a display that, based on the optical image formed by the optical-image forming part, displays distributions of the adipose layer and the surrounding tissue or a boundary therebetween in the optical image, wherein the optical-image forming part is provided with an imaging portion that, of reflected light reflected at the biological tissue due to the illumination light radiated by the light source, captures reflected light in a wavelength band in which an absorption characteristic of β-carotene is greater than an absorption characteristic of hemoglobin, thus acquiring a reflected-light image, wherein the imaging portion acquires a first reflected-light image and a second reflected-light image by capturing first reflected light based only on a first wavelength band within a range from 450 to 500 nm, where the absorption characteristic of β-carotene is greater than the absorption characteristic of hemoglobin, and second reflected light based only on a second wavelength band within a range from 500 to 600 nm, where the absorption characteristic of hemoglobin is greater than the absorption characteristic of β-carotene, by making a distinction between the two,
wherein the imaging portion acquires a third reflected-light image by capturing third reflected light based only on a third wavelength band within a range from 600 to 650 nm, where the absorption characteristic of β-carotene and the absorption characteristic of hemoglobin are both low, by making a distinction from the first reflected-light image and the second reflected-light image, and
the display displays a combined image formed by combining the first reflected-light image, the second reflected-light image, and the third reflected-light image by using different colors.

2. The biological observation apparatus according to claim 1, further comprising:
a mode switching portion that can switch between a first observation mode for capturing reflected light based only on a wavelength band in which, in a blue wavelength band, the absorption characteristic of β-carotene is greater than the absorption characteristic of hemoglobin and a second observation mode for capturing reflected light in all wavelength bands from blue to red.

3. The biological observation apparatus according to claim 2, further comprising:
   a magnification switching portion that can switch an observation magnification,
   wherein the mode switching portion switches to the first observation mode when the magnification switching portion switches the observation magnification to a high magnification and to the second observation mode when the magnification switching portion switches the observation magnification to a low magnification.

4. The biological observation apparatus according to claim 1, wherein the optical characteristic is a spectral characteristic.

5. The biological observation apparatus according to claim 1, wherein the imaging portion captures reflected light in a wavelength band within a range from 450 to 500 nm.

6. The biological observation apparatus according to claim 1, wherein the light source radiates illumination light based only on a wavelength band in which the absorption characteristic of β-carotene is greater than the absorption characteristic of hemoglobin.

7. The biological observation apparatus according to claim 1, wherein the light source separately radiates first illumination light based only on the first wavelength band and second illumination light based only on the second wavelength band.

8. The biological observation apparatus according to claim 1, wherein the light source separately radiates first illumination light based only on the first wavelength band, second illumination light based only on the second wavelength band, and third illumination light based only on the third wavelength band.

9. The biological observation apparatus according to claim 1, wherein the light source radiates illumination light in wavelength bands including the first wavelength band to the third wavelength band at the same time, and
   the imaging portion is provided with a color CCD.

10. The biological observation apparatus according to claim 1, wherein the light source radiates illumination light in wavelength bands including from the first wavelength band to the third wavelength band at the same time, and
   the imaging portion is provided with a spectroscopic part for spectrally separating reflected light from the biological tissue into reflected light in a first wavelength band, a second wavelength band, and a third wavelength band and three imaging devices that separately capture the reflected light in the first to third wavelength bands spectrally separated by the spectroscopic part.

* * * * *